United States Patent [19]

Friese et al.

[11] Patent Number: 5,773,894
[45] Date of Patent: Jun. 30, 1998

[54] INSULATION LAYER SYSTEM FOR THE ELECTRICAL ISOLATION CIRCUITS

[75] Inventors: Karl-Hermann Friese, Leonberg; Heinz Geier, Stuttgart; Werner Gruenwald, Gerlingen; Claudio De La Prieta, Stuttgart, all of Germany

[73] Assignee: Robert Bosch GmbH, Stuttgart, Germany

[21] Appl. No.: 769,182

[22] Filed: Dec. 18, 1996

Related U.S. Application Data

[63] Continuation of Ser. No. 495,488, filed as PCT/DE94/01397, Nov. 26, 1994, abandoned.

[30] Foreign Application Priority Data

Dec. 9, 1993 [DE] Germany .......................... 43 42 033.8
Dec. 8, 1994 [DE] Germany .......................... 44 39 883.2

[51] Int. Cl.[6] ...................... G01N 27/406; G01N 27/407; H01B 3/12; C04B 35/48
[52] U.S. Cl. .......................... 257/760; 204/426; 204/425; 204/429; 204/427; 204/408; 427/126.3; 427/126.4; 264/618; 257/701
[58] Field of Search ..................... 257/701–703, 257/705, 414, 760; 204/424–428, 429, 408; 264/618; 427/125, 126.3, 126.4, 96

[56] References Cited

U.S. PATENT DOCUMENTS

| | | | |
|---|---|---|---|
| 4,107,019 | 8/1978 | Takao et al. | 324/29 |
| 4,296,148 | 10/1981 | Friese et al. | 427/125 |
| 4,462,890 | 7/1984 | Touda et al. | 204/425 |
| 4,507,394 | 3/1985 | Mase et al. | 501/94 |
| 4,559,126 | 12/1985 | Mase et al. | 204/425 |
| 4,798,693 | 1/1989 | Mase et al. | 204/425 |
| 5,169,512 | 12/1992 | Weidenmann et al. | 204/426 |
| 5,169,513 | 12/1992 | Mase et al. | 204/429 |
| 5,670,032 | 9/1997 | Friese et al. | 204/424 |

FOREIGN PATENT DOCUMENTS

| | | |
|---|---|---|
| 0133820 | 3/1985 | European Pat. Off. . |
| 0189038 | 7/1986 | European Pat. Off. . |
| 0203351 | 12/1986 | European Pat. Off. . |
| 2746381 | 4/1978 | Germany . |
| 3811713 | 10/1989 | Germany . |
| 4303633 | 8/1994 | Germany . |

OTHER PUBLICATIONS

Abstract for Japan Kokai Pub. #02–186254, Jul. 1990, 2 pages.
Abstract for Japan Kokai Pub. #03–090851, Apr. 1991, 1 page.
Abstract for Japan Kokai Pub. #03–142351, Jun. 1991, 1 page.

*Primary Examiner*—Tom Thomas
*Assistant Examiner*—Alexander Oscar Williams
*Attorney, Agent, or Firm*—Spencer & Frank

[57] ABSTRACT

An insulation layer system, in particular for gas sensors, is proposed, having at least one electrically conductive solid-electrolyte layer (10), an electrically conductive layer (20) and at least one electrically insulating layer (13) between the solid-electrolyte layer (10) and the electrically conductive layer (20). The material of the insulating layer (13) contains, prior to sintering, pentavalent metal oxides of niobium or tantalum as an additive, it being possible for the additive to diffuse into the adjoining solid-electrolyte layer (10) during sintering.

13 Claims, 4 Drawing Sheets

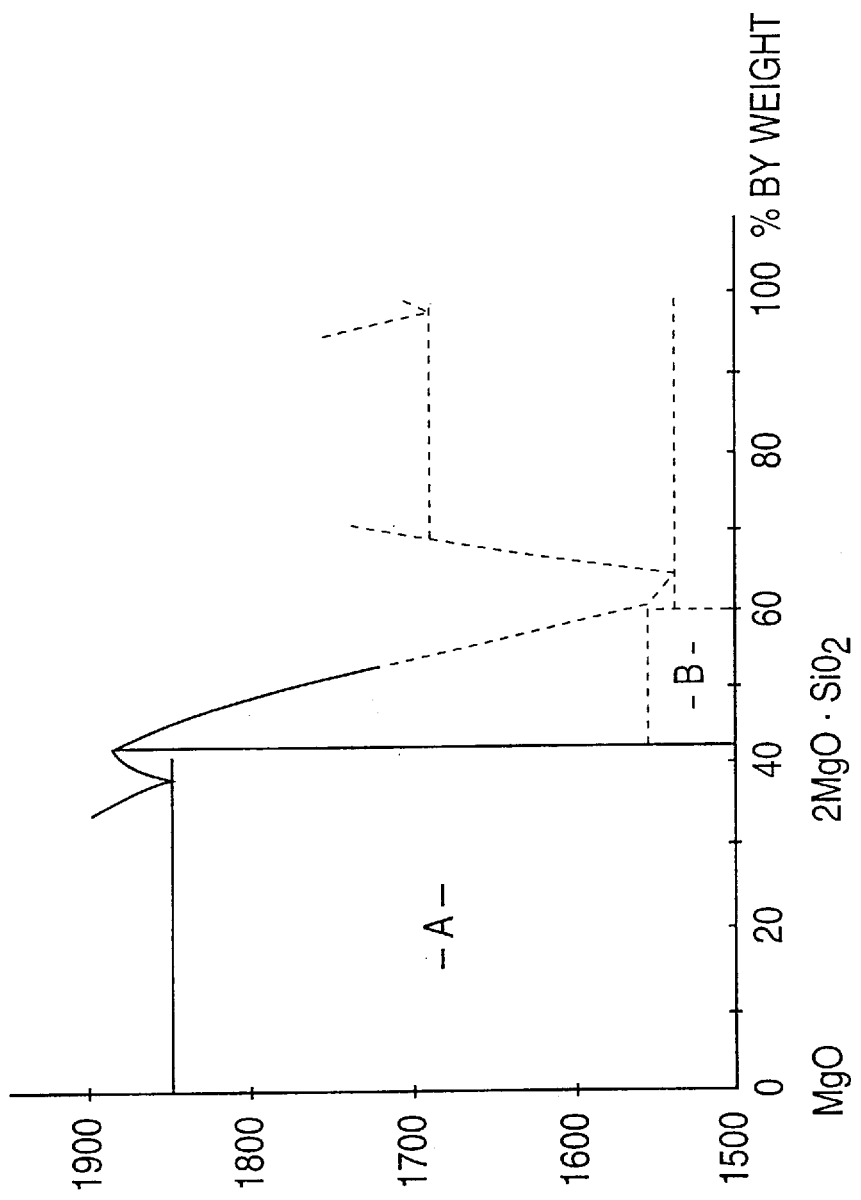

INSULATION LAYER SYSTEM FOR THE ELECTRICAL ISOLATION CIRCUITS

This application is a Continuation of application Ser. No. 08/495,488, filed as PCT/DE94/01397, Nov. 26, 1994, now abandoned.

PRIOR ART

The invention relates to an insulation layer system for the electrical isolation of electric circuits, having an electrically conductive solid-electrolyte layer, an electrically conductive layer and at least one electrically insulating, ceramic layer between the solid-electrolyte layer and the electrically conductive layer. Layer systems of this type are used in gas sensors based on solid electrolytes which are coupled to a heating device. An insulation layer system for gas sensors is disclosed in EP-A0 189 038. A matching layer, for example, is arranged in order to electrically insulate a ceramic solid-electrolyte substrate made of $ZrO_2$ from an electrically conductive heating element. The matching layers of layer systems of this type comprise a mixture of $ZrO_2$ and $Al_2O_3$. The electrical insulation effect remains unsatisfactory.

The object of the invention is to provide an insulation layer system having improved insulation properties and good heat transfer to the solid electrolyte.

SUMMARY ADVANTAGES OF THE INVENTION

The above object generally is achieved according to the present invention by an insulation layer system for the electrical isolation of electric circuits, having an electrically conductive solid-electrolyte layer, an electrically conductive layer and at least one electrically insulating, ceramic layer between the solid-electrolyte layer and the electrically conductive layer, with the material of at least one of the insulating layers being provided with pentavalent metal oxides of niobium or tantalum as additives prior to sintering.

The insulation layer system according to the basic concept of the invention has the advantages that the electrical isolation between the solid-electrolyte layer and the electrically conductive layer is improved without increasing the layer thickness of the insulating layer. The simultaneous improvement in the insulating effect is achieved by the fact that pentavalent cations of the additive diffuse into the host lattice of the solid-electrolyte layer during the sintering process.

Advantageous developments of the layer system specified in the main claim are possible as a result of the measures listed in the subclaims. It is particularly advantageous to select a quantitative ratio of the additive in which, on the one hand, an insulating effect is achieved in the solid-electrolyte layer but, on the other hand, the ion conductivity of the solid electrolyte is not impaired beyond all measure. $Nb_2O_5$ has proved to be a particularly suitable additive in conjunction with a $ZrO_2$ solid electrolyte. It is particularly advantageous for a good thermal shock resistance if the thermal expansion coefficients of the solid-electrolyte layer and the insulating layer are matched to one another. This can be done, on the one hand, by inserting a matching layer between the solid-electrolyte layer and the insulating layer, which matching layer contains material constituents of the solid-electrolyte layer and of the insulating layer. Another possibility is to select the material of the insulating layer in such a way that the thermal expansion coefficient of said insulating layer approaches, i.e., is at least 90% of, the thermal expansion coefficient of the solid-electrolyte layer. A material of this type is, for example, forsterite or forsterite/periclase. However, it is perfectly conceivable to select for the insulating layer a material which has a higher thermal expansion coefficient than of the material of the solid-electrolyte layer. This takes account of the fact that solid electrolytes withstand compressive stresses better than tensile stresses.

An embodiment having very good heat transfer is achieved if the heating element is embedded between two insulating layers, of which the insulating layer facing the sensitive region has a higher thermal conductivity than the further insulating layer facing away from the sensitive region. The consequence of this is intensified heat conduction in the direction of the sensitive region of the gas sensor.

By matching the sintering shrinkage and the thermal expansion coefficient of the insulating layer and the solid-electrolyte layer, it is achieved that the thermal shock resistance is increased and instances of crack formation in the insulating layer and/or in the solid-electrolyte layer are avoided.

A further embodiment is produced by having more than one matching layer. If the mixtures of the material constituents of each matching layer are suitably selected, the concentration profiles of the individual material constituents of the matching layers are formed more rapidly and in an improved manner during sintering.

BRIEF DESCRIPTION OF THE DRAWINGS

Exemplary embodiments of the invention are illustrated in the drawing and explained in more detail in the following description.

FIG. 4 shows a diagrammatic sectional illustration of a gas sensor and FIG. 5 shows a MgO—$SiO_2$ phase diagram.

DETAILED DESCRIPTION OF THE EXEMPLARY EMBODIMENTS

Figure 1:
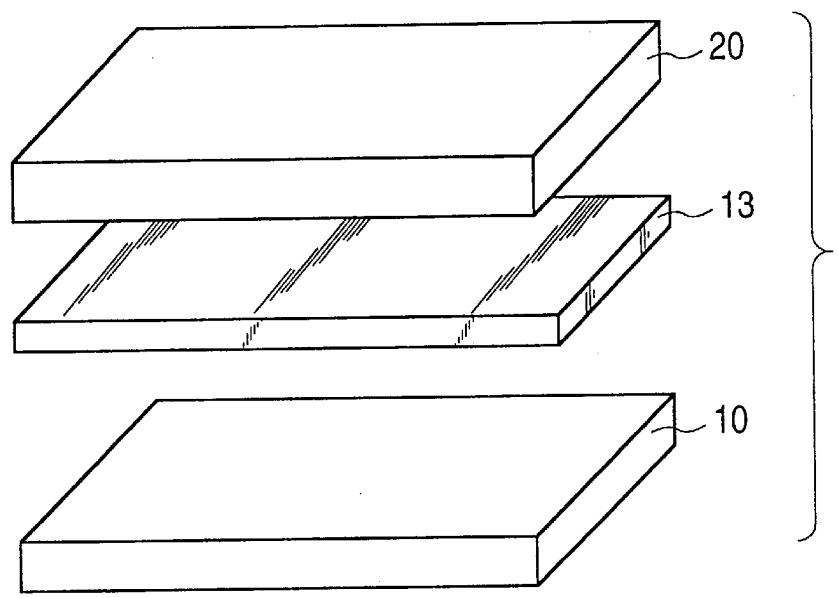
FIG. 1 shows a layer system of a first embodiment.

The insulation layer system according to FIG. 1 comprises a solid-electrolyte layer 10, an electrically conductive layer 20 and an insulating layer 13 in between. This planar layer system forms, for example, the basic structure of a planar gas sensor, in which the solid-electrolyte layer 10 is a $Y_2O_3$-stabilized $ZrO_2$ solid electrolyte. The insulating layer 13 comprises, for example, $Al_2O_3$, to which up to 5% by volume of $Nb_2O_5$ or $Ta_2O_5$ is added prior to sintering. The electrically conductive layer 20 is, for example, a resistive track comprising metals, metal alloys or electrically conductive ceramics. The further functional elements of the gas sensor are not illustrated in FIG. 1.

The layers illustrated in FIG. 1 are laminated together and subsequently sintered at 1200° to 1500° C. In the process, the $Nb^{5+}$ or $Ta^{5+}$ cation of the $Nb_2O_5$ or $Ta_2O_5$ contained in the insulating layer 13 diffuses into the adjoining solid-electrolyte layer 10 and forms a doping region in the boundary area of the solid-electrolyte layer 10, with the effect that the electrical resistance of the solid-electrolyte material is increased in this region.

It is thereby possible to increase the insulation effect of the insulating layer 13 without increasing its layer thickness. A larger layer thickness of the insulating layer 13 would in actual fact impair the adhesive strength between the insulating layer 13 and the solid-electrolyte layer 10 and the heat conduction between the electrically conductive layer 20 and the solid-electrolyte layer 10.

Figure 2:
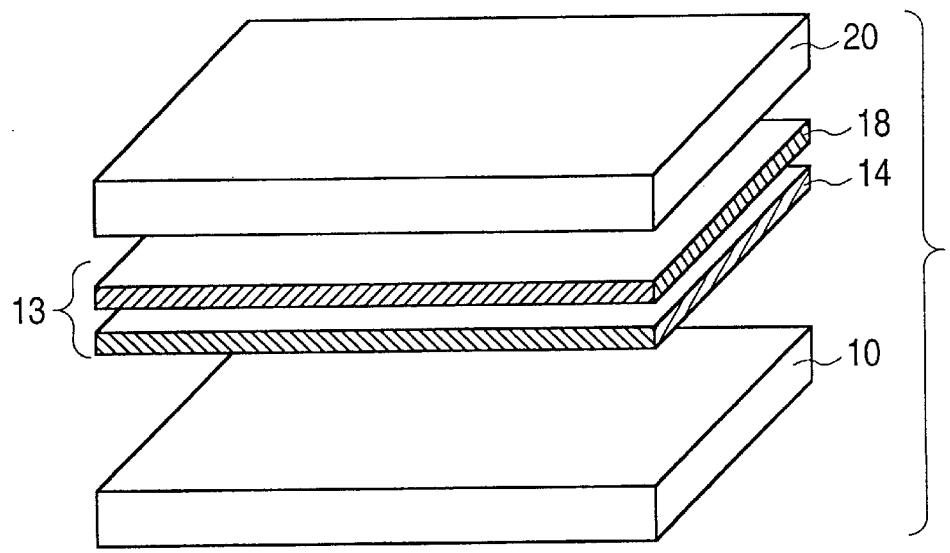
FIG. 2 shows a layer system of a second embodiment with two matching layers.

The electrically conductive layer 20 has a different thermal expansion coefficient in comparison with the solid-electrolyte layer 10 made of stabilized $ZrO_2$ ceramic or $HfO_2$ ceramic. In order to make the thermal expansion coefficients more alike, the insulating layer 13 is made of an insulating layer 18 and of a matching layer 14 formed as shown in FIG. 2, between the solid-electrolyte layer 10 and the electrically conductive layer 20.

The chemical composition of the layers of the insulating layer 13 emerges from the following Table 1, the volumetric ratios for the preparation being set prior to sintering. The parentheses around $Nb_2O_5$ mean that up to 5 percent by volume of $Nb_2O_5$ replaces the $ZrO_2/Al_2O_3$ mixture of the insulating layer 13 (samples 1) and of the matching layers 14, 15 and the insulating layer 18 (samples 2 and 3). All the figures refer to the volume of the mixtures to be prepared.

TABLE

| Layers | 13 | 14 | 15 | 18 |
|---|---|---|---|---|
| Sample 1 (FIG. 1) | $Al_2O_3$ ($Nb_2O_5$) | | | |
| Sample 2 (FIG. 2) | | 50:50 $ZrO_2$:$Al_2O_3$ ($Nb_2O_5$) | | $Al_2O_3$ |
| Sample 3 (FIG. 3) | | 70:30 $ZrO_2$:$Al_2O_3$ ($Nb_2O_5$) | 30:70 $ZrO_2$:$Al_2O_3$ ($Nb_2O_5$) | $Al_2O_3$ |
| Sample 4 | forsterite ($Nb_2O_5$) | | | |
| Sample 5 | 70:30 forsterite: ($Nb_2O_5$) | MgO | | |

Figure 3:
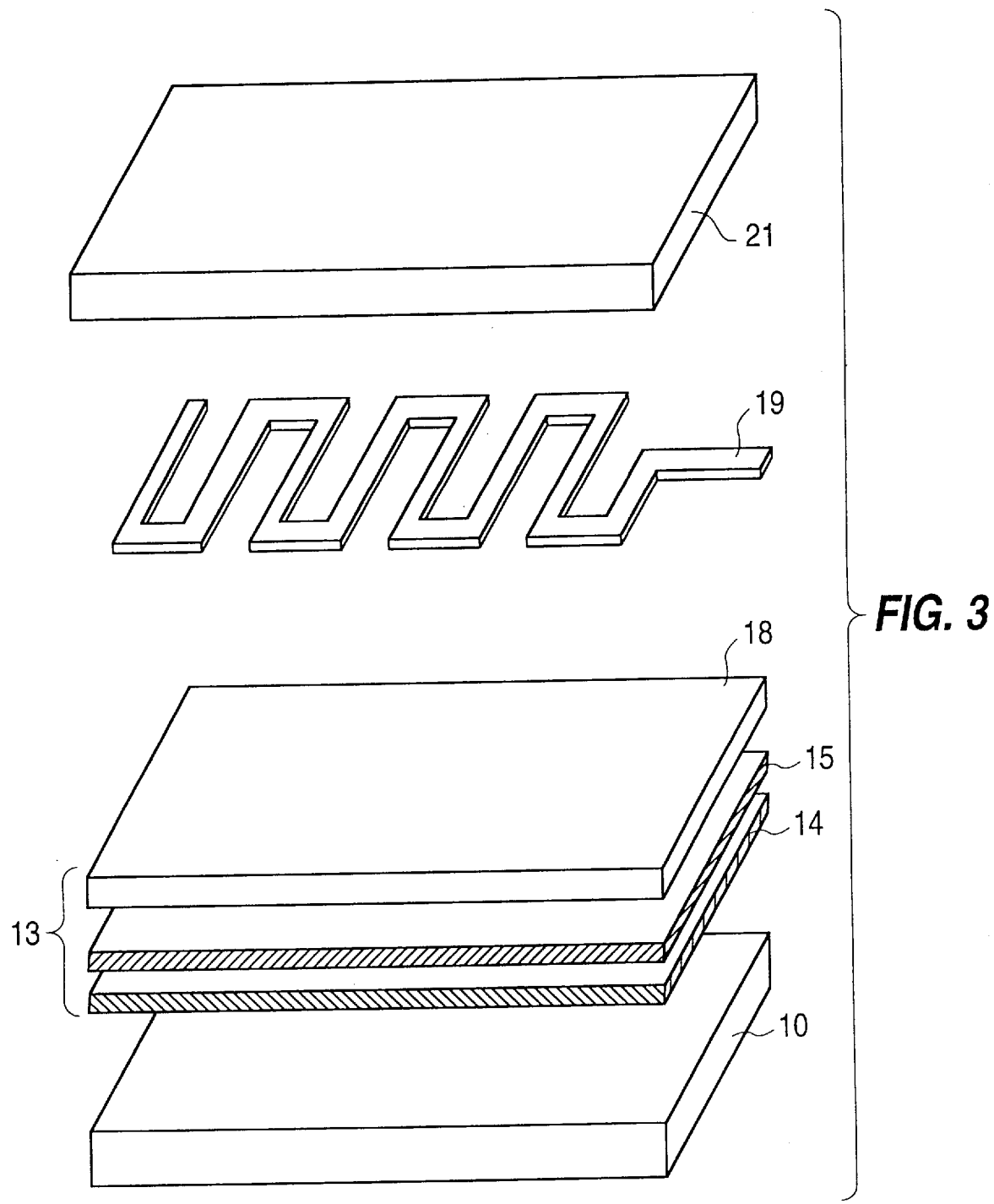
FIG. 3 shows a layer system of a third embodiment with a heating element in a substrate.

A further exemplary embodiment of an insulation layer system emerges from FIG. 3, in the case of which a heating element 19 is provided as the electrically conductive layer 20. Furthermore, the layer system here has two matching layers 14 and 15 for setting the concentration profiles of $ZrO_2$ and $Al_2O_3$ and an insulating layer 18. The insulating layer 13 comprises the layers 14, 15 and 18. The heating element 19 is covered by a mechanical protective layer 21 made of insulating material, for example $Al_2O_3$.

In order to match the thermal expansion coefficient, the matching layer 14 comprises a mixture of the material of the solid-electrolyte layer 10, the main constituent, and the material of the insulating layer 18, the secondary constituent, that is to say expediently comprises a mixture of $ZrO_2$ and $Al_2O_3$ with the additive $Nb_2O_5$ or $Ta_2O_5$. The concentration of the additive may be made to increase toward the solid-electrolyte layer 10.

The matching layers 14 and 15 were designed in such a way that a layer separation of at least 10 micrometers is produced, for a planar layer system, between the solid-electrolyte layer 10 and the electrically conductive heating conductor 19, said layer separation being formed at least by the matching layers 14 and 15 and an insulating layer 18. In the case of the exemplary embodiment of sample 3 according to FIG. 3, it is equally conceivable to admix the $Nb_2O_5$ additive only to the second matching layer 15, but the $Nb_2O_5$ in the matching layer 15 has no influence on the resistance of the substrate 10 after sintering. The same applies to the insulating layer 18 of sample 3 and of sample 2.

It is conceivable to design the layer system using any desired geometry, for example using curved layers as occurs in the case of finger-type probes. It is furthermore conceivable to arrange the matching layers between a $ZrO_2$ layer and an electrode protective layer.

The production of the layer system according to the invention is to be explained using the third exemplary embodiment (FIG. 3, sample 3). In a first step, the first matching layer 14, which is made of 70 parts by volume of zirconium dioxide and 30 parts by volume of aluminum oxide, together that is 95 percent by volume of the material of the first matching layer 14, and 5 percent by volume of $Nb_2O_5$, and has a thickness of 5 micrometers, is printed onto the solid-electrolyte layer 10, for example a $ZrO_2$ substrate (green sheet or pressed). In a second step, a second matching layer 15, for example a layer which is made of 30 parts by volume of zirconium dioxide and 70 parts by volume of aluminum oxide, together that is 95 percent by volume of the material of the matching layer 15, and 5 percent by volume of $Nb_2O_5$, and has a thickness of 5 micrometers, is printed onto the layer system (10, 14) consisting of two layers. In a third step, the insulating layer 18, which is made, for example, of pure aluminum oxide, is applied to the layer system consisting of three layers (10, 14, 15). The insulating layer 13 can have the additive $Nb_2O_5$ present in a quantative ratio of up to 10% by volume of the insulating layer. Finally, the electrically conductive heating conductor 19 made of cermet or electrically conductive ceramic and an insulating $Al_2O_3$ covering layer 21 are also added. Alternatively, the heater may also be embedded into a layer system toward the top. In a concluding fifth step, the layer system (10, 14, 15, 18, 19, 21) is sintered to completion at 1000 degrees Celsius in one of the usual furnaces.

Table 1 contains those examples of the various insulation layer systems which are most suitable for achieving the object. For optimum equalization of the thermal stresses and good adhesion of the layers of the four-ply layer system and of the five-ply layer system (without the covering layer 21), respectively, of FIGS. 2 and 3, the insulating layer 13 should not be significantly thicker than 10 micrometers in order to ensure adequate heat flow from the heating element 19 toward the solid-electrolyte layer 10. Quartz sand and alkaline earth metal oxides were used as the flux.

Figure 4:
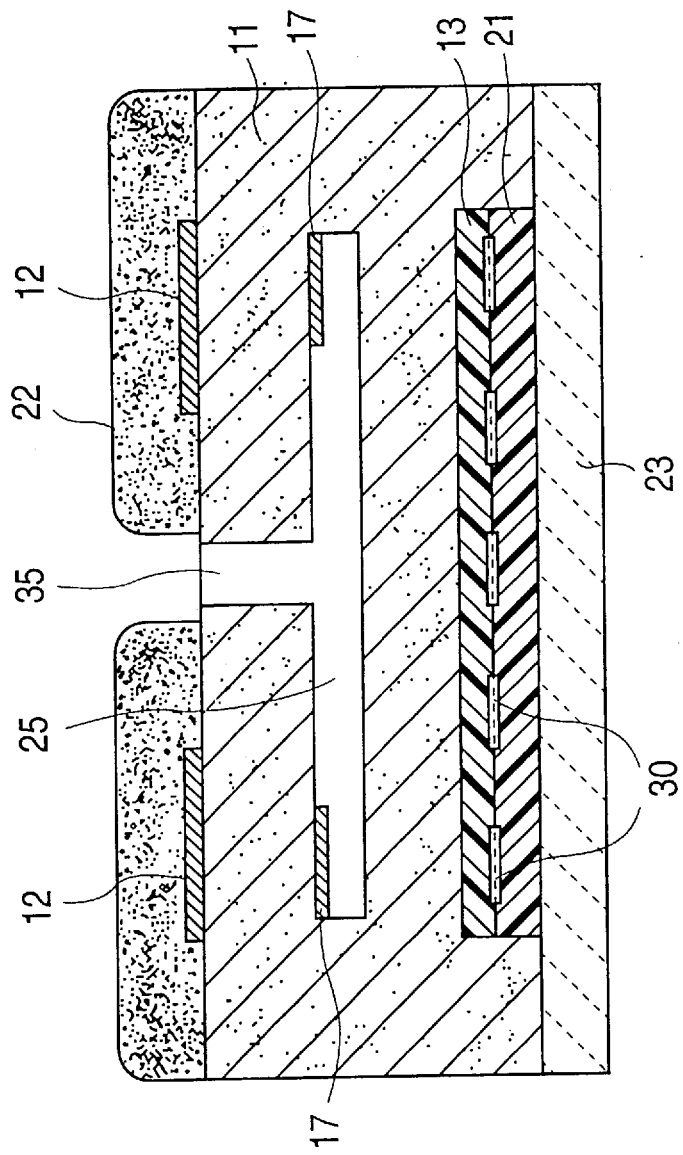

The solid-electrolyte sensor illustrated in FIG. 4 is a gas sensor which is used to determine the oxygen content in gases, in particular in exhaust gases of internal combustion engines. It functions in accordance with the limiting-current principle, which has already been described in DE-A-38 11 713.

The gas sensor has an oxygen ion-conducting solid electrolyte 11, having an outer pumping electrode 12 and an inner pumping electrode 17. The solid-electrolyte body 11, which comprises yttrium-stabilized zirconium dioxide in the present example, is constructed, for example, from a plurality of laminae or sheets. A cavity which forms a flat cylindrical diffusion gap 25 is formed in the solid electrolyte 11, the gas to be measured being conducted to the diffusion gap 25 via a diffusion channel 35. The pumping electrodes 12 and 17 are expediently formed in a ring around the diffusion channel 35 and comprise a porous material, such as platinum or platinum cermet, for example, which catalyzes the gas to be measured. The outer pumping electrode 12 is preferably covered with a porous protective layer 22.

A heating element 30 is positioned between an insulating layer 13 which faces the pumping electrodes 12, 17 and an insulating layer 21 which faces away from the pumping electrodes 12, 17. The insulating layer 21 is adjoined by a ceramic carrier 23 which is, for example, likewise a solid-electrolyte sheet.

Reference is made to DE-A-38 11 713 for the production of the gas sensor. The solid-electrolyte sheets used and the screen-printing steps implemented for producing the individual layers and electrodes are described there.

It is likewise conceivable to use the described exemplary embodiment for electrochemical measuring cells which operate in accordance with the Nernst principle. The difference in comparison with the pumping cell is only that the diffusion gap 25 is fed via a reference channel to a reference gas, for example air. In the case of measuring cells of this type, one electrode is exposed to the gas to be measured and the other electrode is exposed to the reference gas. These measuring cells, too, are implemented with a heating element, with the result that the described problem between the insulating layer and the solid electrolyte exists here as well. The same applies to so-called broadband sensors, which have a Nernst cell and a pumping cell.

FIG. 5 shows a MgO—SiO$_2$ phase diagram according to Bowen and Andersen, *Am. J. Sci.* [41], 37, 488 (1914) with the forsterite phase 2MgO.SiO$_2$. The forsterite in solid form occurs here in the phase areas A and B. The forsterite and the periclase/forsterite eutectic, which is present in the phase area A, have a thermal expansion coefficient which is suitable for the insulating layers 13 and 21 in relation to the yttrium-stabilized ZrO$_2$ solid electrolyte 11. A composition of 70% by weight of forsterite and 30% by weight of periclase is particularly suitable. To the left of the phase diagram, the thermal expansion coefficient of the MgO.SiO$_2$ phases decreases toward the SiO$_2$. In this respect, the region between forsterite and SiO$_2$ is of secondary importance for the invention. Therefore, the phase diagram is indicated by a dashed line there.

As a further embodiment, it is possible to implement the insulating layer 21 facing away from the sensitive region from a material which has a lower thermal conductivity than the material of the insulating layer 13 facing the sensitive region. This produces a specific heat flow in the direction of the sensitive region with the pumping electrodes 12, 17. Such an insulating layer 21 in combination with an insulating layer 13 made of a forsterite/periclase eutectic with 70% by weight of forsterite and 30% by weight of periclase is, for example, a pure forsterite layer or a forsterite layer with a relatively small proportion of periclase (for example <5% by weight).

The usual purity requirements are made of the materials of the insulating layer 13, such as, for example, a very low content of electron-conducting and of ion-conducting materials. In addition, the sintering activity of the insulating layers 13, 21 can be matched by appropriate flux additions. The sintering activity of the insulation layers can be controlled by the selection of the raw materials, for example by mixtures of MgO, SiO$_2$ and Mg silicates in suitable mixture ratios and grain sizes. In order to avoid undesirably intense sintering reactions between the insulating layer 13 and the solid electrolyte 11, the solid electrolyte 11 can be produced by the use of a coprecipitated or at least precalcined yttrium-stabilized ceramic and/or by the selection of materials for the insulating layer 13 which have a cation radius which differs from the Zr$^{4+}$ ion radius.

The following Table 2 shows a survey of the thermal expansion coefficients, the thermal conductivity and the cation radius of various materials for insulating layers in comparison with yttrium-stabilized zirconium dioxide.

| | Thermal expansion coefficient | Thermal conductivity | Cation radius |
|---|---|---|---|
| | 10$^{-6}$ (°C.$^{-1}$) | | ri (A) |
| MgO | 11.6–10.5 | >Al$_2$O$_3$ | Mg$^{2+}$:0.66 |
| CaO | 12.6 | <Al$_2$O$_3$ | Ca$^{2+}$:0.99 |
| SrO | 13.5 | <<Al$_2$O$_3$ | Sa$^{2+}$:1.12 |
| BaO | >10 | <<Al$_2$O$_3$ | Ba$^{2+}$:1.34 |
| 2MgO SiO$_2$ | 9.8–10.6 | <<Al$_2$O$_3$, >>PSZ/FSZ | Mg$^{2+}$:0.66 |
| La$_2$O$_3$ | 12–13 | <<Al$_2$O$_3$ | La$^{3+}$:1.06 |
| Nd$_2$O$_3$ | >10 | <<Al$_2$O$_3$ | Nd$^{3+}$:0.995 |
| Gd$_2$O$_3$ | >10 | <<Al$_2$O$_3$ | Gd$^{3+}$:0.94 |
| Dy$_2$O$_3$ | >10 | <<Al$_2$O$_3$ | Dy$^{3+}$:0.91 |
| Y$_2$O$_3$ stab. ZrO$_2$ | | | |
| PSZ with >20% m-ZrO$_2$ | 9.0–9.8 | <<Al$_2$O$_3$ | |
| PSZ with >95% t-ZrO$_2$ | 10.0–10.8 | <<Al$_2$O$_3$ | Zr$^{4+}$:0.79 |
| FSZ with 7.8 m/o Y$_2$O$_3$ | 10.0–10.8 | <<Al$_2$O$_3$ | |
| >98% Al$_2$O$_3$ | 7–8 | | |
| 90–96% Al$_2$O$_3$ | 7.0–7.6 | >98% Al$_2$O$_3$ | Al$^{3+}$:0.51 |
| Mg spinel | 8.8 | <Al$_2$O$_3$ | Mg$^{2+}$:0.66 |
| MgO Al$_2$O$_3$ | 8.1 | | |
| | | | Nb$^{5+}$:0.70 |
| | | | Ta$^{5+}$:0.73 |

As already mentioned, a forsterite/periclase eutectic was selected as an advantageous exemplary embodiment. The thermal expansion coefficient corresponds to the thermal expansion coefficient of yttrium-stabilized ZrO$_2$. Corresponding combinations of yttrium-stabilized zirconium dioxide and insulating layers can be selected from Table 2, it being important in the selection that the thermal expansion coefficient of the insulating layer 13 is at least approximately equal to or greater than the thermal expansion coefficient of the stabilized zirconium dioxide. It is additionally expedient to take account of a correspondingly good thermal conductivity in the selection. Although the thermal conductivity of the cited materials is without exception less than that of Al$_2$O$_3$, it is still greater than that of the stabilized zirconium dioxide.

A further parameter in the selection of the materials for the insulating layer is the cation radius of the material used. By selecting a cation radius which differs to an appropriate degree from the Zr$^{4+}$ ion radius, it is ensured that an undesirably intense sintering reaction between the insulating layer 13 and the solid-electrolyte body 10 does not occur.

We claim:

1. An insulation layer system for the electrical isolation of electric circuits, having an electrically conductive solid-electrolyte layer, an electrically conductive layer and at least one electrically insulating, ceramic layer between the solid-electrolyte layer and the electrically conductive layer, and wherein: the at least one insulating layer disposed adjacent to the solidelectrolyte layer is formed of an electrically insulating ceramic material, with said insulating ceramic material additionally containing pentavalent metal oxides of niobium or tantalum as an additive in a quantitative ratio of up to 10% by volume with reference to the volume of the at least one insulating layer; and the solid-electrolyte layer has a diffused region doped with pentavalent cations of niobium or tantalum adjacent to an insulating layer, caused by the diffusion of the pentavalent cations from the at least one insulating layer during sintering.

2. The layer system as claimed in claim 1, wherein the ceramic material of at least one insulating layer comprises aluminum oxide, forsterite, a forsterite/periclase eutectic, MgO, CaO, SrO, BaO, 2MgO.SiO$_2$, La$_2$O$_3$, Nd$_2$O$_3$, Gd$_2$O$_3$ or Dy$_2$O$_3$ or a mixture of these materials.

3. The layer system as claimed in claim 2, wherein the at least one insulating layer comprises a ceramic material whose thermal expansion coefficient is at least 90% of the thermal expansion coefficient of the solid-electrolyte layer.

4. The layer system as claimed in claim 2, wherein the thermal expansion coefficient of the insulating layer is greater then or equal to the thermal expansion coefficient of the solid-electrolyte layer.

5. The layer system as claimed in claim 1, wherein the at least one insulating layer comprises an insulating layer disposed adjacent the conductive layer and at least one matching layer for matching the thermal coefficient of expansion of the solid-electrolyte layer to that of the insulating layer disposed adjacent the conductive layer, with the at least one matching layer being arranged adjoining the solid-electrolyte layer and wherein the additive is contained at least in the matching layer adjacent to the solid-electrolyte layer.

6. The layer system is claimed in claim 5, wherein the at least one matching layer contains material constituents of the solid-electrolyte layer and of the insulating layer.

7. An insulation layer system for the electrical isolation of electric circuits, having an electrically conductive solid-electrolyte layer, an electrically conductive layer and at least one electrically insulating, ceramic layer between the solid-electrolyte layer and the electrically conductive layer, and wherein: the at least one insulating layer comprises a ceramic insulating layer disposed adjacent the conductive layer and a ceramic matching layer, with the matching layer being arranged adjoining the solid-electrolyte layer; the matching layer contains the material constituents of the solid-electrolyte layer and of the ceramic insulating layer in equal volumetric proportions; and at least the ceramic material of the matching layer adjacent to the solid-electrolyte layer contains pentavalent metal oxides of niobium or tantalum as an additive.

8. An insulation layer system for the electrical isolation of electric circuits, having an electrically conductive solid-electrolyte layer, an electrically conductive layer and at least one electrically insulating, ceramic layer between the solid-electrolyte layer and the electrically conductive layer, and wherein: the at least one insulating layer comprises a ceramic insulating layer disposed adjacent the conductive layer and a plurality of ceramic matching layers of varying material composition disposed between the ceramic insulating layer and the solid-electrolyte layer; the matching layer contains the material constituents of the solid-electrolyte layer and of the ceramic insulating layer, with the concentration of the material constituent of the solid electrolyte layer increasing toward the solid-electrolyte layer; and, at least the ceramic material of one of the plurality of matching layers adjacent to the solid-electrolyte layer contains pentavalent metal oxides of niobium or tantalum as an additive.

9. The layer system as claimed in claim 8, wherein the concentration of the additive increases toward the solid-electrolyte layer.

10. The layer system as claimed in claim 1, wherein a further insulating layer is provided in addition to the ceramic insulating layer, and wherein a heating element is arranged between the ceramic insulating layer and the further insulating layer.

11. An insulation layer system for electrical isolation in a gas sensor, with the layer system having an electrically conductive solid-electrolyte layer, an electrically conductive layer and an electrically insulating, ceramic layer between the solid-electrolyte layer and the electrically conductive layer, and wherein: the material of the ceramic insulating layer contains pentavalent metal oxides of niobium or tantalum as an additive; a further insulating layer is provided in addition to the insulating layer; a heating element is arranged between the insulating layer and the further insulating layer; and, the insulating layer facing a sensitive region of a gas sensor has a higher thermal conductivity than the insulating layer facing away from the sensitive region.

12. The layer system as claimed in claim 1, wherein the solid-electrolyte layer comprises at least one of stabilized zirconium dioxide and stabilized hafnium dioxide, with one of diyttrium trioxide and diytterbium trioxide being present for the purpose of stabilization.

13. The layer system as claimed in claim 1 wherein the additive is present in a quantitative ratio of up to 5% by volume relative to the volume of the ceramic insulating layer.

* * * * *